United States Patent [19]
Bowers

[11] Patent Number: 6,122,954
[45] Date of Patent: Sep. 26, 2000

[54] HIGH SENSITIVITY INSTRUMENT TO MEASURE NVR IN FLUID

[75] Inventor: William D. Bowers, Newport Beach, Calif.

[73] Assignee: Femtometrics, Inc., Irvine, Calif.

[21] Appl. No.: 09/138,043

[22] Filed: Aug. 21, 1998

Related U.S. Application Data

[63] Continuation of application No. 08/678,792, Jul. 11, 1996, Pat. No. 5,918,258.

[51] Int. Cl.$^7$ .............................. H03H 9/25; G01N 29/02; G01N 29/22
[52] U.S. Cl. ................... 73/24.06; 73/31.06; 310/313 R; 310/313 D
[58] Field of Search ................................ 73/24.01, 24.06, 73/31.06, 32 A, 54.41, 599, 61.79; 310/313 D, 313 B, 313 R, 312

[56] References Cited

U.S. PATENT DOCUMENTS

| | | | |
|---|---|---|---|
| 3,715,911 | 2/1973 | Chuan | 73/24.03 |
| 3,915,645 | 10/1975 | Funke et al. | 73/24.01 |
| 4,307,356 | 12/1981 | Arai | 310/313 D |
| 4,518,944 | 5/1985 | Faris | 310/343 |
| 4,561,286 | 12/1985 | Sekler et al. | 73/24.06 |

(List continued on next page.)

FOREIGN PATENT DOCUMENTS

| | | |
|---|---|---|
| 4-14884 | 5/1992 | Japan. |
| 1681229 A1 | 9/1991 | U.S.S.R.. |

OTHER PUBLICATIONS

Reprint from instrument & control systems, *Testing Small Orifices*, James M. Benson, Charles E. Hawk, Hastings Raydist, Inc Charles Evans & Associate Brochure, *Time-of-Flight Secondary Ion mass Spectrometer*.

Reprint from Ultra Water Journal, Jul./Aug. 1994, *The Measurement of Nonvolatile Residue in High-Purity Water and Clean Liquids*.

Particle Measuring Systems, Inc. Brochure, *LiquiTrak Nonvolatile Residue Monitors For Liquids*.

The International Society for Optical Engineering, *Optical System Contamination: Effects, Measurement, Control III*, Jul. 23–24, 1992

(List continued on next page.)

*Primary Examiner*—Hezron Williams
*Assistant Examiner*—Rose M. Miller
*Attorney, Agent, or Firm*—Knobbe, Martens, Olson, & Bear, LLP

[57] ABSTRACT

A real time nonvolatile residue (NVR) monitor operates to efficiently detect molecular contamination in a given environment. The present NVR monitor utilizes surface acoustic wave (SAW) resonators in a controlled environment which efficiently promotes deposition of NVR on the sensor surface. The SAW resonators preferably operate at a resonant frequency of approximately 200 MHz–2,000 MHz which enables the NVR monitor to detect molecular contamination on the order of $10^{-11}$ g-cm$^{-2}$ to $10^{-13}$ g-cm$^{-2}$. The NVR monitor utilizes active temperature control of (SAW) resonators to achieve a stable resonant frequency and to thermally separate NVR from a sample fluid contacting the SAW. The temperature control system of the NVR monitor is able to directly heat and cool the SAW resonators utilizing a thermoelectric element to maintain the resonators at a preset temperature in accordance with optimal environmental conditions for separating NVR from the sample fluid. The sample fluid, comprising a carrier fluid and NVR, is furthermore processed to provide conditions, such as precooling and/or pressurization, which enhance condensation of NVR on the sensor surface. Increasing the collection efficiency allows the NVR monitor to operate faster at a desired level of accuracy and provides more quantitative information for trace contaminant analysis.

40 Claims, 8 Drawing Sheets

U.S. PATENT DOCUMENTS

| | | | |
|---|---|---|---|
| 4,596,286 | 6/1986 | Ballato | 73/24.06 |
| 4,599,532 | 7/1986 | Okamoto et al. | 310/313 D |
| 4,683,394 | 7/1987 | Koshino | 310/313 R |
| 4,792,939 | 12/1988 | Hikita et al. | 370/277 |
| 4,895,017 | 1/1990 | Pyke et al. | 73/24.06 |
| 4,917,499 | 4/1990 | Champetier et al. | 374/14 |
| 4,932,255 | 6/1990 | Brace et al. | 73/24.03 |
| 5,012,668 | 5/1991 | Haworth | 73/24.06 |
| 5,042,288 | 8/1991 | Vig | 73/24.01 |
| 5,076,094 | 12/1991 | Frye et al. | 73/19.03 |
| 5,117,146 | 5/1992 | Martin et al. | 310/313 R |
| 5,138,869 | 8/1992 | Tom | 73/31.03 |
| 5,175,711 | 12/1992 | Shiba et al. | 310/313 D |
| 5,194,830 | 3/1993 | Fleischmann | 310/313 D |
| 5,221,871 | 6/1993 | Fuchs et al. | 310/313 R |
| 5,223,762 | 6/1993 | Masaie et al. | 310/313 D |
| 5,243,539 | 9/1993 | Holt et al. | 702/30 |
| 5,289,715 | 3/1994 | Staples et al. | 73/24.01 |
| 5,325,704 | 7/1994 | Mariani et al. | 73/24.06 |
| 5,325,705 | 7/1994 | Tom | 73/31.03 |
| 5,476,002 | 12/1995 | Bowers et al. | 73/24.01 |
| 5,550,062 | 8/1996 | Wohltjen et al. | 436/155 |
| 5,571,944 | 11/1996 | Pfeifer et al. | 73/24.04 |
| 5,661,226 | 8/1997 | Bowers et al. | 73/24.01 |

OTHER PUBLICATIONS

American Institute of Physics, *A 200 MHz Surface Acoustic Wave Resonator Mass Microbalance*, Feb. 4, 1991.

American Institute of Physics, *Surface Acoustic–Wave Piezoelectric Crystal Aerosol Mass Microbalance*, Apr. 3, 1989

National Aeronautics and Space Administration, *KCS Payload Facility Contamination Control Requirements/Plan* Nov. 1987.

Elsevier Sequoia, *Mechanism of Operation, and Design Considerations for Surface Acoustic Wave Device Vapour Sensors*, May 21, 1994

Journal of Spacecraft and Rockets, vol. 17, No. 2, *Miniature Quartz Crystal Microbalance for Contamination Measurement*, Mar.–Apr., 1990.

Analytical Chemistry, vol. 51, No. 9, Aug. 1979, *Surface Acoustic Wave Probes for Chemical Analysis. III. Thermomechanical Polymer Analyzer.*

Analytical Chemistry, vol. 51, No. 9, Aug. 1979, *Surface Acoustic Wave Probes for Chemical Analysis. II. Gas Chromatograph Detector.*

Analytical Chemistry, vol. 51, No. 9, Aug. 1979, *Surface Acoustic Wave Probe for Chemical Analysis. I. Introduction and Instrument Description.*

Applied Physics Letters, vol. 7, No. 12, Dec. 15, 1995, *Direct Piezoelectric Coupling to Surface Elastic Wave.*

Education for Technical Excellence, Annual Technical Meeting, May 1–6, 1994 *Real–Time SAW Measurements of NVR in Cleanroom and in Microenvironment.*

NASA Technical Memorandum, 1993, *Research and Technology 1993 Annual Report.*

Howard W. Sams & Company, *Modern Dictionary of Electronics*, Sixth Edition.

HIGH SENSITIVITY INSTRUMENT TO MEASURE NVR IN FLUID

This is a continuation of application Ser. No. 08/678,792, filed Jul. 11, 1996, now U.S. Pat. No. 5,918,258.

BACKGROUND OF THE INVENTION

1. Field of the Invention

The present invention relates to a contamination monitor for fluids, and more specifically, to a contamination monitor which is capable of measuring fluid contamination at the molecular level in real-time.

2. Description of the Related Art

The cleanliness requirements for the manufacture and operation of sophisticated technical systems are becoming ever more stringent. This is especially true in manufacturing processes involved in microelectronics, high precision optics, as well as in the preparation of systems for flight of spacecraft. It is no longer sufficient just to maintain a certain level of particulate matter in a work environment, as has been the practice for several decades; it is becoming clear that contamination on a molecular level can create serious manufacturing and operational problems.

It is well known that all materials and most activities emanate gases or small aerosols by diffusion and desorption. The term "contamination" refers to a situation where an emitted gas or aerosol impinges and condenses on a surface. Contamination of a "clean" surface typically originates from two main sources: activities or processes in the clean work area and from the materials used in the construction of the article itself (self-induced contamination).

Nonvolatile residue (NVR), sometimes referred to as molecular contamination, on critical surfaces surrounding space structures have been shown to have a dramatic impact on the ability to perform optical measurements from platforms based in space. In such cases, the particulate and NVR contamination originate primarily from pre-launch operations. Molecular deposition on such surfaces affects the thermal balance of a spacecraft scheduled for a long duration mission since the absorbance and emittance of the thermal control panels are adversely affected. Any optical surface (such as windows or mirrors) is degraded by molecular depositions and particulates. Condensed films of contaminants on the order of 10 angstroms thick degrade the efficiency and operation of the optical components. Therefore, a real-time measurement of NVR is required to assure that critical components are fully operational and not subjected to high levels of contaminants during payload processing, storage or on-orbit.

In microelectronics fabrication, the ability to manufacture higher performance and higher density integrated circuits places stringent demands on the physical and chemical properties of materials used. Clearly, as integrated circuit path dimensions shrink to the far sub-micron regime with thinner thicknesses of oxide and metal layers, contamination on a molecular level will have substantial adverse effects. Thus, contamination must be monitored during product processing as well as in process fluids (liquids and gasses) before and during their use.

The currently accepted Semiconductor Equipment Manufactures Institute (SEMI) standard method of measuring NVR in liquids is based on a weight residue technique. The major drawbacks to this method is that it is time consuming, tedious and is not very sensitive. An aliquot of the process fluid is placed in the pre-weighed dish and the sample liquid evaporated to dryness. The weight of the remaining residue is considered NVR and is expressed in parts per million (ppm). The lower limit of detection is around 5 ppm. Other disadvantages of this method is several hundred milliliters of sample are required per assay and the evaporating vapors must be contained and not released into the environment, especially if the process liquid is toxic. A method which requires 1000 times less of the process liquid for each assay and be performed in a few minutes would be advantageous.

Another method to measure NVR in process liquids is based on forming a small aerosol droplets of the process liquid and suspending them in a gas stream to accelerate the evaporation of the liquid. After the liquid has evaporated, any NVR material forms small particles which are detected by an optical counter. The number of particle counts is related to the concentration of NVR material. This technique uses less solvent and is, in general, less time consuming per assay than the weight residue method. However, the instrumentation is extremely sophisticated and known to require highly technical operators to achieve the best performance. The major disadvantage of this technique is that the correlation of NVR deposition on a semiconductor surface from the liquid using particles counts is questionable and not straight forward.

A piezoelectric crystal microbalance has been used for the measurement of mass deposition. Piezoelectric crystals in this category have operated in the bulk-vibration mode wherein the entire body of the crystal is driven electrically into resonance. The piezoelectric crystal operates as a microbalance by the de-tuning of the crystal's resonant frequency when mass is added to its surface.

U.S. Pat. No. 4,561,286 issued to Sekler, et al., discloses such a bulk piezoelectric crystal microbalance. The bulk-vibration method requires the placement of the resonating electrodes on the opposite side of the bulk crystal, wherein the distance between the electrodes, i.e., the thickness of the crystal, defines the resonating frequency of the crystal. Therefore, the resonant frequency of a bulk vibration crystal is inversely proportional to the crystal thickness. The limit of the resonant frequency obtained with a bulk mode crystal is approximately 15 MHz, because a thinner crystal would be too fragile. Since the change in mass detectable by the crystal is proportional to the square of its frequency, the limit of mass resolution in the bulk vibration mode is typically on the order of $10^{-8}$ to $10^{-9}$ g-cm$^{-2}$. This level of mass resolution is sufficient to detect contamination at a particle level but is not fine enough to detect contamination at a molecular level.

U.S. Pat. No. 5,476,002, issued to Bowers, et al., which is incorporated herein by reference, discloses a high-sensitivity, ambient, real-time NVR monitor capable of detecting contamination at the molecular level with greater mass sensitivity than previously reported. The greater mass sensitivity was obtained using piezoelectric crystals having a resonant frequency at 200 MHz. The relationship between frequency and mass may be defined mathematically. For example, the change in frequency due to mass addition AM, over area A, follows the general form, $$\Delta f = -\alpha f_o^2 \Delta M / A \tag{1}$$

The coefficient $\alpha$ depends on the type of crystal and the mode in which its oscillation is excited by the application of an electric field. For a quartz crystal operating in the thickness-shear mode (for an AT-cut bulk crystal), $$\Delta f = -2.2 \times 10^{-6} f_o^2 \, \Delta M / A \tag{2}$$

Since the mass sensitivity is a function of the square of the fundamental oscillating frequency, small increases in the operating frequency give greater performance. However, with the standard bulk crystal operating in the shear mode, as the operating frequency increases, the thinner the crystal must be. A trade-off of mass sensitivity versus crystal ruggedness results in a 10 MHz crystal being the most commonly used as a microbalance as it possesses acceptable mechanical strength with a mass sensitivity around $4.42 \times 10^{-9}$ gm/Hz cm² (equivalent to $2.3 \times 10^8$ Hz cm²/gm).

Higher resonating frequencies can be achieved by driving the crystal in a surface acoustic mode, wherein the top few atomic layers of the piezoelectric crystals surface are driven in a longitudinal acoustic mode by a series of closely spaced interdigitated electrode transducers which are deposited on the surface of the crystal substrate. The electric field is applied parallel to the surface of the crystal and Rayleigh waves are generated which move along the surface of the crystal. The fundamental frequency of this device is mainly dependent on the configuration of the transducers and not on the thickness of the substrate. Therefore, higher operating frequencies can be achieved without reducing the thickness of the crystal.

Surface acoustic wave (SAW) piezoelectric sensors typically used by researchers in analytical applications are based on SAW delay lines. When two sets of interdigital electrodes are deposited on a piezoelectric crystal at a distance L apart, a standing wave is set up if $L=N\lambda$, where N is an integer and $\lambda$ is the wavelength of the surface acoustic wave. The frequency f is equal to $v/\lambda$ where v is the surface acoustic wave phase velocity. The wavelength is dependent on the spacing, s, between the interdigital electrodes, and is equal to twice the spacing. The bandwidth of the device is determined by the length of each transducer. The transducers serve two main functions, the first is to convert electrical energy from the oscillator circuit into mechanical energy on the surface of the quartz piezoelectric crystal, and vise versa. The second function is to establish the frequency response of the delay line. The Rayleigh surface wave travels in both directions away from the transducer. The surface wave that travels away from the opposite transducer and towards the end of the crystal is lost which results in the delay line being a low Q device. Clearly, a high Q device would provide greater mass-loading dynamic range and possess higher frequency stability.

A factor which limits the lower limit of detection of NVR material in fluids is the probability that 100% of the contaminants present in a sample fluid will deposit or adsorb onto the surface of the SAW device during the time the fluid comes in contact with the sensor. The collection efficiency of a SAW device is influenced by the probability of a given molecular species being adsorbed, the so-called "sticking coefficient." A priori such factors in general are not well-known, but clearly a low collection efficiency will contribute to the time necessary for a reliable measurement. Moreover, for quantitative trace analysis, uncertainty in the collection efficiency can substantially limit the precision of an assay.

Ideally, NVR fluid monitoring should proceed in real-time, and yet a variety of noise sources conspire to increase the time necessary to reach a desired level of accuracy. Clearly, there exists a need for a real-time NVR monitor which can take fill advantage of the great sensitivity offered by state-of-the-art SAW devices.

Such a NVR monitor could operate with microliter liquid sample sizes that provide a true measure of NVR deposition. The high sensitivity of such instrument would permit real-time analyses and thus could be used as process control instrument.

SUMMARY OF THE INVENTION

The present invention comprises an apparatus for detecting contamination in fluids. The apparatus comprises a SAW sensor having a sensor surface. A fluid inlet receives a mixture of contaminants and an otherwise pure fluid from an external source. A fluid dispenser receives the mixture from the inlet and dispenses the mixture onto the sensor surface. In the preferred embodiment, a first temperature controller is in thermal contact with the SAW sensor, and a fluid dispenser disposed adjacent to the sensor surface directs a sample fluid onto the sensor surface. The sample fluid may be either a liquid or a gas. Preferably, the dispenser is arranged to direct the sample fluid in a substantially linear path from the fluid dispenser to the sensor surface. In one embodiment, the dispenser comprises a conduit which delivers a gas through an orifice, and in another embodiment the dispenser comprises an array of jets disposed in close proximity to the sensor surface. The temperature controller may comprise a heat sink and thermal contact with the SAW sensor and a thermoelectric element for heating and cooling the heat sink.

According to another aspect of the invention, a method of detecting contaminants in a fluid comprises the step of inputting a mixture of the fluid and contaminants onto a surface of a SAW sensor. The mixture is transported along a flow path to a SAW sensor without separating the contaminants from the fluid, and the mixture is directed onto a surface of the SAW sensor. The contaminants are thermally separated from the fluid such that the contaminants are distributed on such surface. Changes in the response of the SAW sensor are detected in order to detect the contaminants in the sample fluid. Preferably, the mixture travels in a substantially linear path from a fluid dispenser to the surface of the SAW sensor. In one embodiment, thermal separation of a gas from contaminants therein is accomplished by maintaining the SAW sensor at a temperature which induces condensation of the contaminants onto the surface of the SAW sensor. In another embodiment, thermal separation of a liquid from contaminants therein is achieved by maintaining the SAW sensor at a temperature sufficient to induce evaporation of the liquid from the surface of the SAW sensor. If desired, the molecular species of the contaminants remaining on the surface of the SAW sensor may be identified by determining a mass spectrum of the molecular species.

Yet another aspect of the invention comprises the step of applying a mixture of contaminants and an otherwise pure liquid onto a surface of a SAW sensor. The contaminants are thermally separated from the liquid such that the liquid is removed from the surface SAW sensor while the contaminants remain. Changes in the response of the SAW sensor are detected to detect the contaminants.

In the preferred embodiments, the contaminants consist of bulk containment contaminants. The term "bulk containment contaminant," as used herein, means a contaminant that contaminates an otherwise pure fluid by virtue of loading the fluid into a bulk containment vessel, storing it in the vessel, or dispensing the fluid from the vessel. An example is a lubricant such as a high molecular weight oil or grease that may become trapped in a valve and becomes mixed with the fluid as it passes through the valve. The contaminant can come from the vessel itself, the transfer line, and any surface the pure fluid contacts as it is loaded, stored, or dispensed. By way of example, the pure fluid may comprise a solvent or cleaning fluid.

DETAILED DESCRIPTION OF THE PREFERRED EMBODIMENT

The preferred embodiment of the present invention comprises an enhanced adsorption NVR monitor that operates under conditions which promote the precipitation or adsorption of NVR on a SAW sensor surface. By increasing the NVR deposition efficiency, a higher mass-loading per unit volume of sample fluid is achieved thereby increasing signal-to-noise ratio. Alternatively, measurements may be made to a desired level of precision in a shorter time period. Furthermore, by creating conditions under which substantially all of the trace contaminants are deposited on the sensor surface for a given amount of sample, a more quantitative trace analysis may be achieved. Thus, the NVR monitor of the embodiment is more accurate and sensitive than its predecessors.

Figure 1:
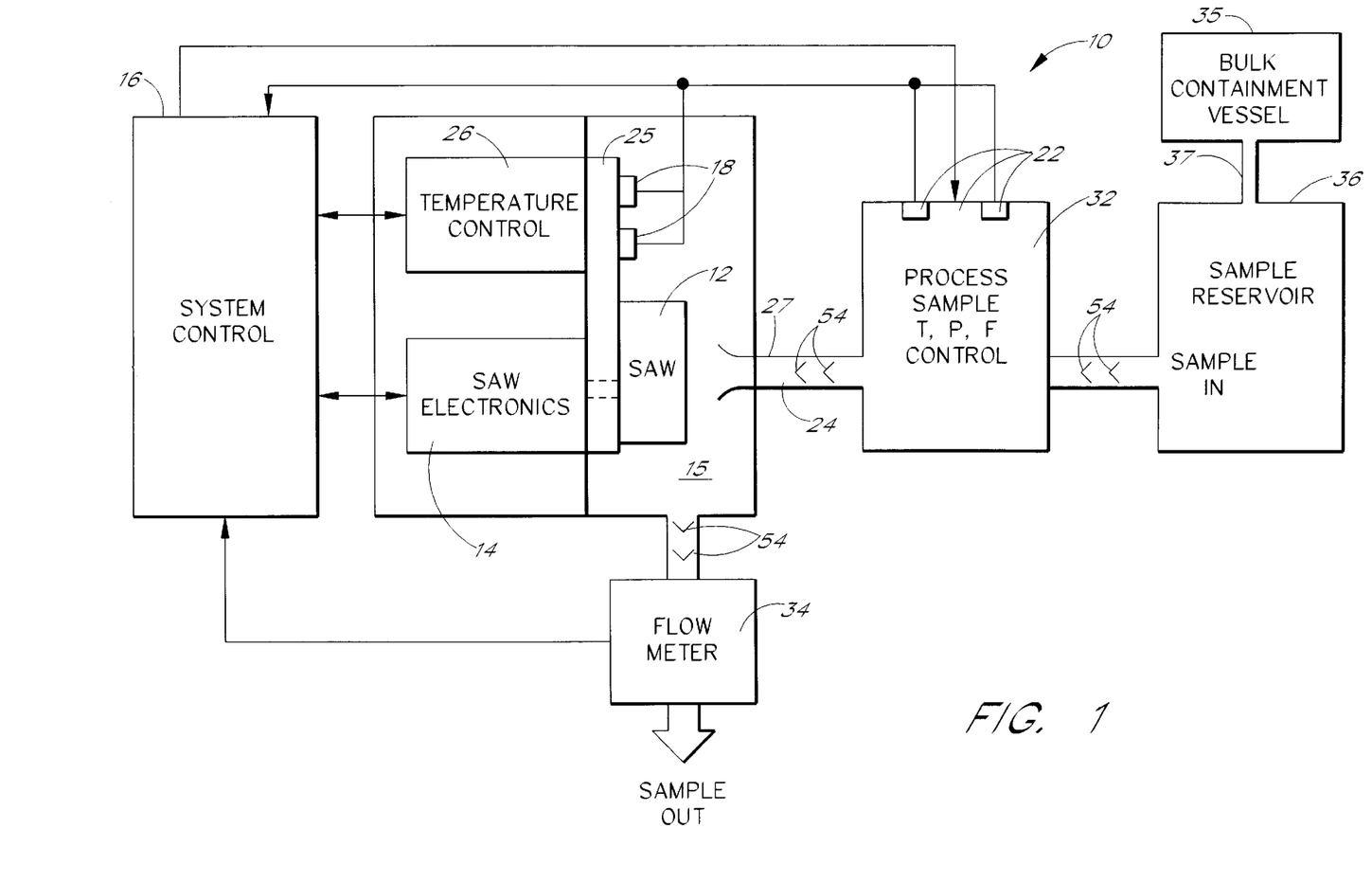
FIG. 1 is a schematic diagram of an embodiment of the NVR monitor of the present invention.

As shown in FIG. 1, one embodiment of the NVR monitor comprises a sensing SAW device 12 or SAW sensor, SAW electronics 14 connected to drive the SAW sensor 12 and a system controller 16 connected to regulate operation of the SAW sensor 12 and receive information from the SAW sensor 12. A temperature controller 26 comprising a heat exchanger (not shown) and heat sink 25 is maintained in thermal contact with the SAW sensor 12. The temperature controller 26 maintains the SAW sensor 12 at a preselected temperature. Additionally, environmental sensors 18 and 22 are provided to determine the environmental conditions, for example temperature, pressure or humidity, in the regions surrounding the SAW sensor 12. A fluid 24, in the form of a liquid or gas, having bulk containment contaminants mixed therein, is stored in a bulk containment vessel 35. Such fluid 24, which in the preferred embodiment comprises a compound of at least two elements, is transported to a sample fluid reservoir 36 by any suitable means such as a conduit or line 37. The sample fluid reservoir 36 is connected to a fluid supply system 32 which adjusts and maintains the optimum conditions for the delivery of sample fluid 24 to the SAW sensor 12. The sample fluid supply system 32 adjusts such delivery conditions as sample fluid temperature (T), pressure (P) and flow (F) prior to delivering the sample fluid 24 to the SAW sensor 12. The sample fluid 24 is directed to the surface of the SAW sensor 12 by a sample fluid conduit 27 such as a pipe or hose and fluid inlet fixture. The conduit 27 in general comprises an arrangement for transferring sample fluid 24 to the surface of the SAW sensor 12 without introducing additional contaminants into the sample fluid 24. Materials which provide minimal self-contamination such as glass, Teflon or stainless steel are suitable for the fluid conduit 27. Preferably the length of the fluid conduit 27 is in the range of a few centimeters or less.

Additionally, the fluid conduit 27 preferably provides a substantially linear path for the flow of the sample fluid 24 from the conduit 27 to the surface of the SAW sensor 12. A flow meter 34 is connected to monitor the amount of sample fluid 24 contacting the SAW sensor 12.

In operation, the SAW sensor 12 is exposed to a flow of sample fluid schematically represented by arrows 54. The sample fluid 24 may for example comprise a substance such as a gas or liquid that contains trace amounts of contaminants to be detected by the SAW sensor 12. The fluid substance, which may be viewed as a "carrier" for the contaminants, is brought into intimate contact with the SAW sensor 12 under conditions which promote deposition of the contaminants onto the surface of the SAW sensor 12. As previously described, mass-loading due to such adsorption causes a change in the frequency response of the SAW sensor 12. Detection and monitoring this response is correlated with the mass-loading and amount of contacting fluid, thereby allowing detection of the NVR and determination of contaminant levels. The process of establishing conditions which promote adsorption of NVR on the SAW sensor 12 may comprise temperature controlling the SAW sensor as well as temperature, pressure and flow controlling the sample fluid 24 in the fluid supply system 32, labelled "Process Sample" in FIG. 1. The environmental sensors 18 and 22, together with the flow meter 34, provide information useful for optimizing the process of efficiently depositing NVR on the sensor 12 and allowing quantitative trace analyses. For example, in the case of sample gases, high efficiency collection of trace contaminants in such sample gases comprise controlling and maintaining the temperature of the SAW sensor 12 at a value which promotes selective adsorption of the contaminants but not the carrier gas that contains the contaminants. More preferably, the temperature, pressure and flow of the sample gas is adjusted, in addition to the SAW temperature to optimize the selective adsorption of contaminants. Another method to improve or optimize the selective adsorption of the contaminants is to alter the chemical nature of the SAW sensor surface. For example, to enhance the adsorption of water vapor (a common contaminant in microelectronics process gas) a hygroscopic polymer (such as polystyrene sulfonic acid) covers the SAW sensor surface. This polymer exhibits preferential adsorption of water as compared to the carrier gas containing the water. Water vapor would be preferentially adsorbed into the polymer resulting in a frequency shift.

For a situation in which contaminants are to be measured in a sample liquid, the temperature of the SAW sensor 12 should be controlled and maintained at a value which promotes selective evaporation of the sample liquid, but not the contaminants.

The NVR monitor may comprise, for example, bulk or surface acoustic wave configurations. However, the preferred embodiments of the present enhanced adsorption NVR monitor utilize an alternative configuration to the SAW delay line, called a SAW resonator. SAW resonators of the type utilized herein are described in U.S. Pat. No. 5,476,002 by W. D. Bowers and R. L. Chuan, which is hereby incorporated herein by reference.

Figure 2:
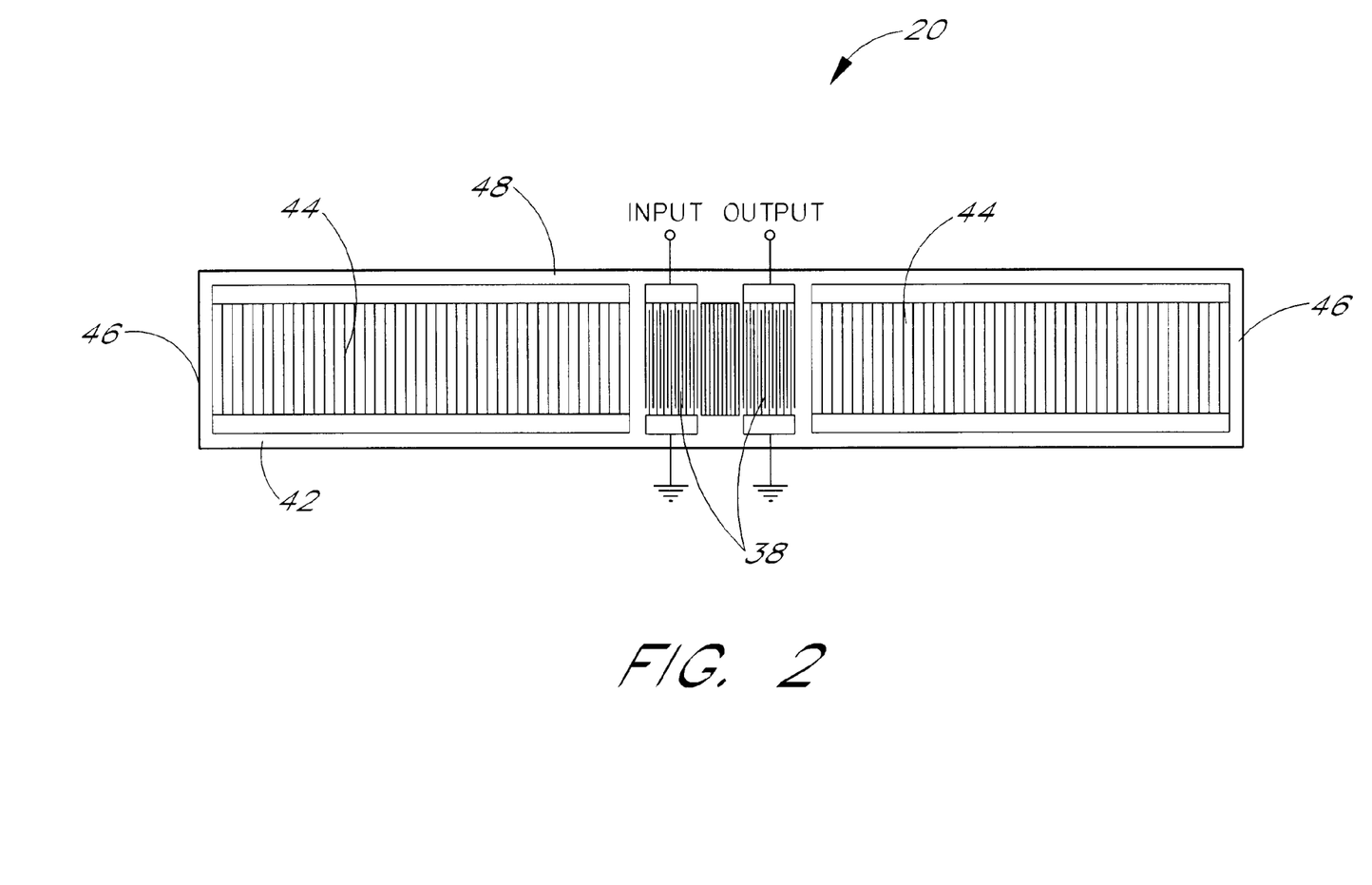
FIG. 2 is a schematic illustration of a SAW resonator utilized in preferred embodiments of the present invention.

As shown in FIG. 2, the SAW sensor 12 may comprise a SAW resonator 20 that operates at a resonant frequency of approximately 200 MHz–2,000 MHz. The SAW resonator 20 is of the type disclosed in an article entitled "A 200 MHz Surface Acoustic Wave Resonator Mass Microbalance," by W. D. Bowers and R. L. Chuan, published in *Rev. Sci. Instrum.*, Vol. 62, pp. 1624 in 1991, which is hereby incorporated by reference. The SAW resonator is similar in construction to a standard SAW delay line with interdigital electrodes deposited onto the surface of an ST quartz substrate, but contains additional passive elements deposited on its surface. The SAW resonator 20 comprises of two transducer electrode arrays 38 that convert the electrical energy into mechanical energy and a set of reflector arrays 44 on each end 46 of the crystal 48. Unlike the delay line, the resonator's frequency of oscillation is determined by the configuration of the reflector arrays 44. The mechanical energy traveling along the surface 42 of the crystal 48 is reflected back towards the transducer 38 setting up a standing wave trapping the acoustic energy within the crystal 48 by the constructive interference of the reflected waves. The resonator 20 is therefore a high Q device since the energy is not lost on the ends 46 of the crystal 48. When a SAW resonator 20 of approximately 200 MHz (e.g., 199.1 MHz) is utilized, an NVR monitor may have a mass sensitivity of about $2 \times 10^{-11}$ gm/Hz cm$^2$ (equivalent to 50 Hz cm$^2$/gm).

Figure 3:
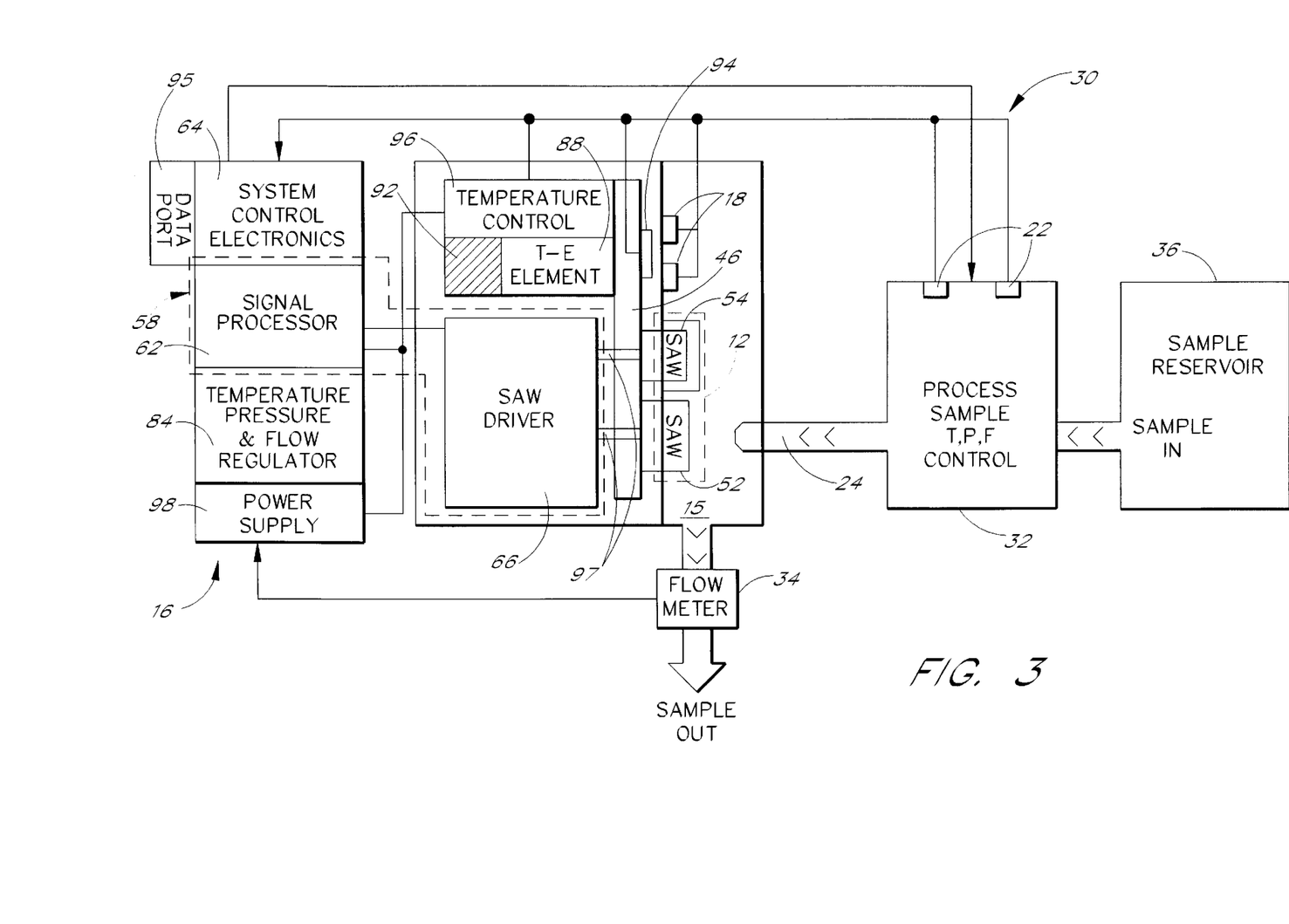
FIG. 3 is a schematic diagram of a preferred embodiment of the NVR monitor of the present invention.
Figure 4:
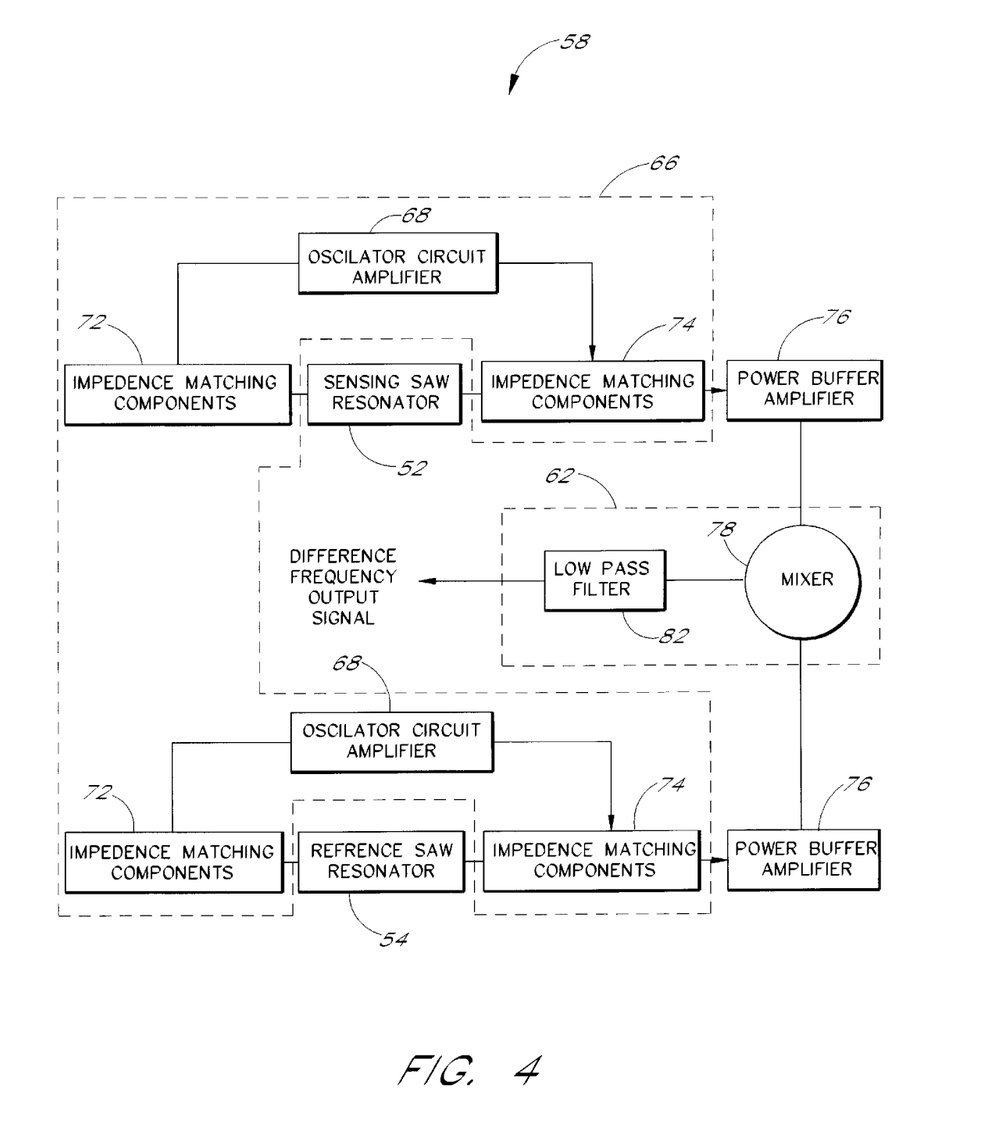
FIG. 4 is a block diagram of preferred SAW control electronics.

Referring to FIGS. 3–4, a preferred embodiment of the NVR monitor 30 preferably operates in the dual difference mode. In the dual difference mode, the SAW sensor 12 comprises two separate SAW resonators, namely, a first sensing resonator 52, also referred to as a detection resonator, and a second reference resonator 54. The sensing resonator 52 is exposed to the sample fluid 24 to measure the NVR contamination that is deposited on its surface. The reference resonator 54 is hermetically sealed for example in a standard electronics package to prevent any contamination from effecting its resonant frequency. Preferably, the reference resonator 54 is matched to the sensing resonator 52 to ensure that the reference resonator 54 has a resonating frequency which is approximately 20 KHz to 300 KHz above the frequency of the sensing resonator 52.

As shown in FIG. 3, the resonators 52, 54 are connected to SAW control electronics 58. An output signal from the sensing resonator 52 is mixed with an output signal from the reference resonator 54 by a signal processor 62 as part of the SAW control electronics 58. The difference or beat frequency is determined and supplied as an output signal to system control electronics 64. By selecting the reference resonator 54 to be at a frequency which is above the frequency of the sensing resonator 52, a decrease in frequency of the sensing resonator 52, due to the deposition of molecules on its surface, is manifested as an increase in the beat frequency from the SAW control electronics 58 supplied to the system control electronics 64. As illustrated in FIG. 4, the SAW control electronics 58 comprises the signal processor 62 and oscillator electronics 66. The oscillator electronics 66 comprises, for each of the resonators 52, 54, an oscillator circuit amplifier 68, a first set of impedance matching components 74 and a second set of impedance matching components 72. The operation of the oscillator electronics 66 will be described hereinafter with reference to the sensing resonator 52; however, it will be understood that a similar set of electronic components are provided for the reference resonator 54 and that these components operate in the same way. In this regard, the oscillator circuit amplifier 68 amplifies the output signal from the sensing resonator 52 to accommodate any signal losses. The output signal from the oscillator circuit amplifier 68 is fed back to the sensing resonator 52 through the first set of impedance matching components 74. The first set of impedance matching components 74 comprises passive components (inductors, capacitors, resistors, etc.), which match the signals from the oscillator circuit amplifier 68 to the input characteristics of the sensing resonator 52 and power buffer amplifier 76. The power buffer amplifier 76 connects each portion of the oscillator electronics 66 to the signal processing electronics 62. A second set of impedance matching components 72 comprises passive components (inductors, capacitors, resistors, etc.), which match the signal from the resonator 52 with the input characteristics of the oscillator circuit amplifier 68. In addition, the power buffer amplifier 76 provides isolation for the oscillator electronics 66 from the signal processing electronics 62. The signal processing electronics 62 comprises a mixer 78, and a low pass filter 82. The output of the signal processing electronics 62 is a difference or beat frequency which is supplied to the system control electronics 64. As discussed hereafter, the system control electronics 64 includes temperature control electronics and signal conducting electronics.

As best illustrated in FIG. 3, the reference resonator 52 is mounted proximal to the sensing resonator 54. Both resonators are thus exposed to the same environmental conditions, which automatically compensates for fluctuations in temperature and pressure caused by the environment in which the SAW resonators 52, 54 are located. In addition, by measuring only the beat frequency rather than the individual frequency of the resonators 52, 54, the resulting beat frequency signal is in the kilohertz range which can be acquired with conventional data acquisition hardware rather than requiring special equipment to measure and transmit the high order frequencies of the individual resonators 52, 54.

In order to guard against false NVR readings due to drastic changes in the environment temperature, the temperature of the SAW resonators 52, 54 is actively controlled apart from the temperature fluctuations in the surrounding environment. By actively controlling the temperature of the SAW resonators 52, 54 to maintain a preset or preselected temperature, temperature changes in the environment will not induce a major drift in the baseline temperature. In this way, the theoretical lower limit-of-detection of a 200 MHz SAW resonator 20, i.e., mass detection on the order of $10^{-11}$ g-cm$^{-2}$, can be realized. In order to accurately control the temperature of the SAW resonators 52, 54, the NVR monitor 30 includes a temperature control system. As shown in FIG. 3, the temperature control system comprises a heat sink 46, a thermoelectric element 88 such as a peltier element, a radiator 92, a temperature sensor 94 and temperature control electronics 96 which are connected to the system control electronics 64. The SAW resonators are mounted to the heat sink 46 so that the temperature control system is able to directly heat and cool the SAW resonators 52, 54 to maintain the resonators at a preset temperature independent of the environmental conditions sensed by sensors 18.

In the embodiment shown in FIG. 3, the sensing SAW resonator 52 is exposed to the sample fluid 24, which may be in the form of an ambient fluid surrounding the NVR monitor in the form of a closed system of gas or liquid. The fluid 24 is input to the chamber 15 by way of a fluid inlet fixture so that it contacts the surface of the sensing SAW resonator 52. As mentioned previously, proximal to the resonators 52, 54 is an array of environmental sensors 18 which monitor certain parameters that influence the manner in which the NVR monitor 30 operates, such as room temperature, humidity, etc. In order to enable the direct heating and cooling of the SAW resonators 52, 54, the SAW resonators 52, 54 are operatively mounted to a heat sink 46, such that one first side of the heat sink 46 physically and thermally contacts the SAW resonators 52, 54. The opposite side of the heat sink 46 is proximal to electronic circuitry which comprises at least a portion of the SAW control electronics 58. Signals are transmitted between the resonators and the electronics 58 via lines 97 that pass through the heat sink 46. This configuration minimizes the distance that high frequency signals to and from the SAW resonators 52 and 54 are transmitted.

A preferred embodiment of the heat sink 46 comprises a configuration which extends between the SAW resonators 52, 54 and the SAW driver electronics 66. Another portion of the heat sink 46 extends past the electronic circuit 66 and physically contacts a first side of a thermoelectric element 88, such as a peltier device. An opposite side of the thermoelectric element 88 is in physical contact with a radiator 92 which assists in the dissipation of excess heat, for example through metal cooling fins.

The thermoelectric element 88 is used to control the temperature of the SAW resonators 52, 54. The operation of the thermoelectric element 88 is controlled by temperature control electronics 96 which operate as an extension of the system control electronics 64. The thermoelectric element 88 acts as both a heating element and as a cooling element depending on the direction of the current which is input to the thermoelectric element 88. If the current is applied in a forward direction, i.e, toward a positive voltage terminal of the thermoelectric element 88, the thermoelectric element 88 acts as a thermal heater. If the current is applied in a backwards direction, i.e., towards a negative voltage terminal of the thermoelectric element 88, the thermoelectric element 88 acts as a thermal cooler. The magnitude of the current which is sent to the thermoelectric element 88 determines the magnitude of the heating or cooling of the SAW resonators 52, 54. The temperature control electronics receives the SAW temperature information from a temperature sensor 94 which is mounted on the heat sink 86 in close proximity to the SAW resonators 52, 54. The temperature detected by the temperature sensor 94 is compared to a stored preset temperature which is the preferred operating temperature of the SAW resonators 52, 54 for a given application. As the NVR monitor 30 can be used to monitor molecular contamination in a variety of different sample fluids 24, the operating temperature is preselected by the user depending on the physical characteristics of the sample fluid 24 and contaminants contained therein which are to be monitored. The temperature control electronics 96 produces a temperature signal which is representative of the temperature difference between the measured temperature and the stored preset temperature. This signal is output from the electronics 96 to a power supply 98. The temperature signal determines the magnitude and direction of a current delivery signal that is sent from the power supply 98 to the thermoelectric element 88 to operate the thermoelectric element 88 in either the cooling or the heating mode.

If the temperature of the SAW resonators 52, 54 is below the preset temperature, the thermoelectric element 88 is operated in the heating mode. When the thermoelectric element 88 is operated in the heating mode, the current which is applied to the thermoelectric element 88 produces heat, the level of which is dependent upon the magnitude of the current. The heat from the thermoelectric element 88 is transferred into the heat sink 46 which is in thermal contact with the thermoelectric element 88. The heat from the thermoelectric element 88 travels along the length of the heat sink 46 to the SAW resonators 52, 54. The thermoelectric element 88 provides such heat via the heat sink 88 until the SAW resonators 52, 54 reach the desired preset temperature.

If the temperature of the SAW resonators 52, 54 is above the preset temperature, the thermoelectric element 88 is operated in the cooling mode. When the thermoelectric element 88 is operated in the cooling mode, the thermoelectric element 88 draws heat from the heat sink 46. The rate at which the heat is drawn from the heat sink 46 is dependent upon the magnitude of the current signal which is applied to the thermoelectric element 88. The heat sink 46 is in thermal contact with the SAW resonators 52, 54 and therefore draws the heat from the SAW resonators 52, 54 and delivers it to the thermoelectric element 88 when it is operating in the cooling mode. The excess heat which is drawn by the thermoelectric element 88 is dissipated though the fins of the radiator 92 which may be cooled by an air stream entering the housing of the NVR monitor or by connecting the heat sink to a large mass to dissipate the heat.

As described above, the heat sink 46 is positioned between the SAW resonators 52, 54 and the electronic circuit board which contains the SAW driver electronics 66. Electrical leads of the SAW resonators 52, 54 are connected through the heat sink 46 to the electronic circuit board via electrical lines in electrical conduits 97. As it is desirous to provide an NVR monitor 30 which is inexpensive to manufacture, in the preferred embodiment of the NVR monitor 30, the SAW resonators 52, 54 are located in close proximity to the SAW driver electronics 66 to eliminate the need for additional circuitry to compensate for the phase shifting, impedance mismatching and losses which may otherwise occur along the electrical path 97. However, it is also desirous to provide a heat sink 46 of sufficient thickness that the heat generated by the SAW resonators 52, 54, the external environment and the internal SAW electronics 58 be dissipated as quickly as possible through the heat sink 46 and away from the SAW resonators 52, 54. Preferably, a heat sink 46 of at least 0.088 inches thick is used to provide a sufficient dissipation of the excess thermal energy. The preferred embodiments of the present invention utilize a heat sink 86 which is approximately 0.088–0.145 inches thick. In one embodiment, a recess of approximately 0.05 inches in depth is formed in the heat sink so that the thickness of the heat sink at the recess is approximately 0.20 inches. The SAW resonators 52, 54 are mounted within the recess of the heat sink 46. The preferred embodiment of the recess has an area that is not substantially larger than the combined area of the SAW resonators 52, 54 such that the heat sink 46 remains sufficiently thick throughout its length to provide good thermal conduction. Preferably, the length of the electrical path 97 between the SAW resonators 52, 54 and the SAW electronics 66 is approximately 0.1 to 0.2 inches.

The NVR monitor 30 outputs the data that it collects via a data port 95 to an external recording and/or processing system (not shown). Types of data which are collected by the NVR monitor 30 include the beat frequency from the sensing 52 and reference 54 resonators (which indicates the level of molecular contamination measured by the NVR monitor 30), the temperature of the SAW resonators 52, 54 (as determined by the temperature sensor 94), and the temperature of the sample fluid contacting the resonator 52 (as determined by the sensors 18), the amount of sample fluid 24 contacting the SAW resonator 52 (as determined by the flow meter 34), and the temperature and pressure of the sample fluid 56 during the process stage 32 (as determined by sensors 22). In one embodiment, the sensors 18 also measure the pressure of the sample fluid contacting the resonator 52. Data signals from these sensors are collected and scaled to signal levels which are accepted by the external recording and/or processing system by signal conditioning electronics which are a part of the system control electronics 64 of the NVR monitor 30. These signals are output through the data port 95 to the external recording and/or processing systems for recording and or analysis.

In addition to maintaining an active temperature control independent of the temperature fluctuations, other precautions are taken to ensure an accurate NVR measurement is achieved. For example, the operational elements of NVR monitor 30 are enclosed such that only the sample fluid 24 may contact the sensing SAW resonator 52. Self-generated contaminants are prevented from entering the sensing chamber.

Figure 5:
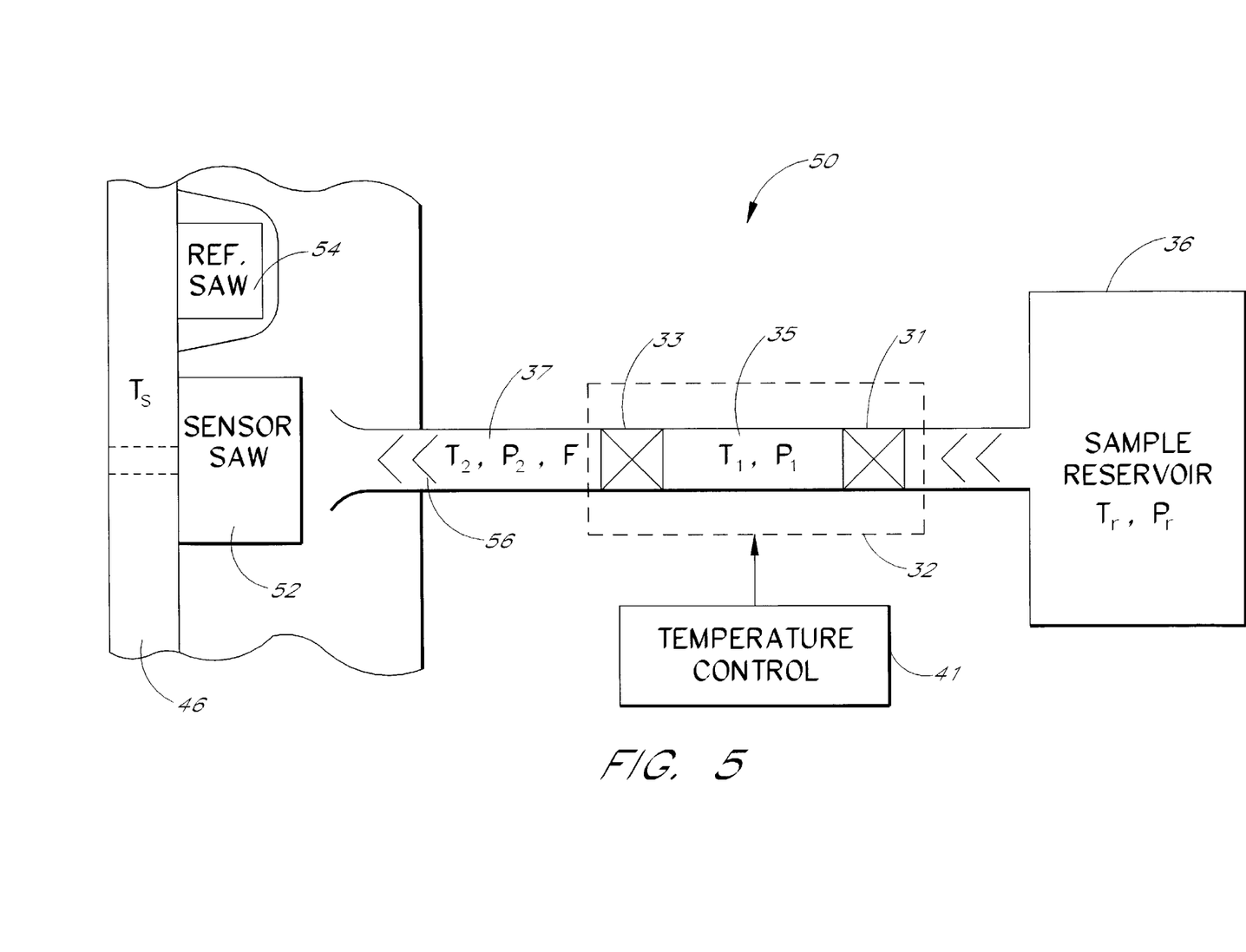
FIG. 5 is a schematic illustration of an embodiment of a gas phase NVR monitor environmental control system.

As described above, the NVR monitor 30 is advantageously used to measure trace contaminants in a variety of sample fluids, including gas. For optimal NVR monitor efficiency, environmental conditions should be controlled and maintained to provide lower noise, higher collection efficiencies, and more accurate knowledge of the collection efficiency for quantitative trace analysis. As shown schematically in FIG. 5, a preferred gas phase NVR monitor 50 comprises the sensing SAW resonator 52 in contact with the heat sink 46 which maintains the SAW sensor 52 at a preselected temperature $T_S$, The reference SAW resonator 54 is also maintained at the preselected temperature $T_S$. A sample gas 56 such as a process gas useful for semiconductor integrated circuit fabrication (for example, $C_2F_6$ or hexafluoroethane) is supplied to the SAW sensor 52 from the sample reservoir 36, which received gas from the bulk containment vessel 35 (FIG. 1). In a preferred embodiment, the gas is a process gas such as $C_2F_6$, $C_2HF_3$, or $CF_4$, which may be used for cleaning or etching electronic products. Additionally, other gases may be used. For example, the gas may be a beverage additive such as $CO_2$. In typical applications, the gas is stored under pressure (at least 100 psi) and is delivered to the reservoir 36 under pressure via a conduit, such as line 37 (FIG. 1). For higher collection efficiency of NVR in the sample gas 56, the temperature, pressure, and flow of the gas is controlled by a process schematically shown in box 32. For example, the sample gas 56 is supplied via the sample reservoir 36 having an initial temperature and pressure $T_r$, $P_r$. A pressure regulator 31 may adjust the pressure in the process 32 to achieve a pressure $P_1$ and an independent temperature controller 41 is used to achieve a temperature $T_1$. The temperature $T_1$, for example, may be maintained at a value which prevents NVR from absorbing on the internal surfaces of the gas supply lines and valves. Valve 33 is a flow controller which may be embodied as an all-metal needle valve. The flow controller 33 controls the amount of gas 56 contacting the SAW resonator 52 in a given period of time, designated here by F. Additionally, the flow controller 33 may also provide adiabatic cooling of the sample gas 56 so that the gas 56 attains a second temperature $T_2$ and pressure $P_2$. While it is not necessary to provide adiabatic cooling of the sample gas 56, it is advantageous from the perspective of cooling the gas 56 without contacting a surface which would allow deposition of NVR. The temperature $T_2$ is therefore preferably less than $T_1$ but still greater than $T_S$. To minimize non-SAW surface contact, the flow controller 33 should be as close as possible to the SAW resonator 52 and positioned such that the sample gas 56 flows directly onto the SAW resonator surface 52, for example by providing a short, line-of-sight flow path as depicted in FIG. 5.

Preferably, the flow controller 33 provides a degree of adiabatic cooling to achieve near 100% collection efficiency of NVR on the SAW resonator 52. For example, the temperature $T_1$ may be high enough to prevent condensation of NVR contaminants, while $T_2$ may be low enough to achieve condensation of NVR contaminants if there were a surface for nucleating such a condensate. The surface of the SAW resonator 52 would then provide an efficient nucleation surface for NVR condensation. It is considered important, therefore, that the flow path from the flow controller 33 to the SAW resonator 52 be as short and direct as possible.

It is believed that this method of cooling the gas, i.e., passing the gas through a narrow constriction having a pressure differential on either side is a substantially isenthalpic process wherein the Joule-Thompson coefficient of the carrier gas may be utilized for determining optimum conditions under which to form the process. Thus, for cooling the gas by passing it through the needle valve 33 it is advantageous to choose conditions where the Joule-Thompson coefficient is positive. Alternatively, the gas may be heated by passing through the valve by choosing conditions under which the Joule-Thompson coefficient is negative.

Other efficient NVR collection protocols are possible using the NVR monitor 50. For example, flow controller 33 may provide precooling of the sample gas 56 to a temperature $T_2$, in which case the SAW resonator 52 may be maintained at a temperature $T_S$ which induces condensation of a fixed amount of sample gas 56. Subsequent to condensation, the temperature $T_S$ may be raised so as to evaporate the carrier gas, leaving only NVR contaminants on the surface. In this way, it is possible to achieve substantially 100% collection efficiency using a known quantity of gas.

Still another advantageous aspect of the present embodiment is the possibility of performing materials characterization of the NVR after it is deposited on the SAW surface. Although a bare SAW surface itself does not provide material-specific information, the NVR monitor is easily adapted to accommodate any of several surface analysis tools. For example, after NVR deposition, the SAW surface may be analyzed by a surface analytic technique capable of distinguishing atomic, chemical, or molecular species. Such techniques as Auger electron spectroscopy, electron energy loss spectroscopy, IR or Raman spectroscopy, or mass spectroscopy are suitable for analyzing the nature of the NVR on the SAW surface. In particular, Time-Of-Flight Secondary Ion Mass Spectroscopy (TOF-SIMS) is presently conceived as a promising candidate for materials characterization of NVR on a SAW surface. Briefly, TOF-SIMS operates by directing a beam of laser light or energetic ions, such as $Ga^+$ ions, onto the SAW surface. The beam energy is transferred to the surface, ionizing and desorbing the molecular species present. These ionized molecules are then analyzed by a TOF mass spectrometer which provides an abundance distribution as a function molecular weight. A TOF-SIMS apparatus suitable for the invention described herein is commercially available through Charles Evans and Associates, Redwood City, Calif. 94063.

Figure 6:
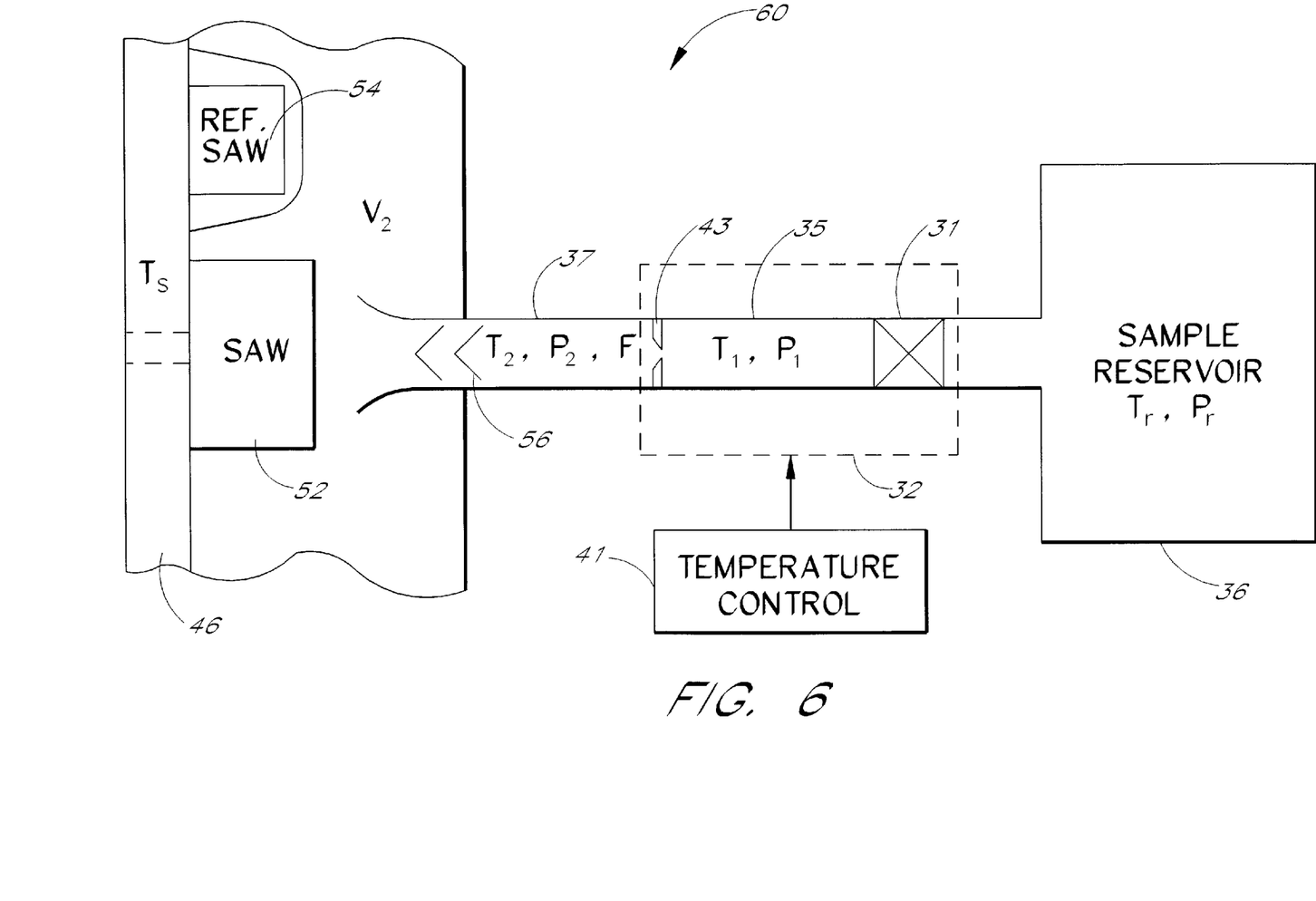
FIG. 6 is a schematic illustration of a preferred embodiment of a gas phase NVR monitor environmental control system.

As shown in FIG. 6, the gas precooling process may be accomplished using a critical orifice 43 in the gas inlet fixture. The orifice 43 may comprise a disk or plate with a small hole having edges that taper outwardly on the downstream side of the gas flow. This configuration significantly reduces surface contact of the gas with the edge surfaces, and thereby prevents buildup of contaminants on such edge surfaces. Preferably, the orifice 43 is positioned in a line-of-sight flow arrangement with the surface of the SAW resonator 52. As previously shown in FIG. 5, the sample gas 56 is transferred from a reservoir 36 through a regulator 31 to obtain an initial pressure P1. The initial temperature T1 is also controlled. The flow F through the orifice 43 will in general depend upon the pressure differential $P_1-P_2$ where $P_2$ may optionally be adjusted by an exhaust pump (not shown). Moreover, adiabatic or isenthalpic expansion occurring in the sample gas 56 as a result of flowing through the orifice 43 will give rise to a temperature change, yielding a final temperature $T_2$. As mentioned previously, the direction and magnitude of temperature change will depend upon the pressure differential $P_1-P_2$, the initial temperature T1 and the Joule-Thompson coefficient for the sample gas under these conditions.

Most preferably, the orifice 43 is operated in the so-called critical regime where the flow F is substantially independent of the downstream pressure P2. When gas flows through a nozzle or orifice, the flow depends on the pressure differential across the orifice only up to a certain point. If the upstream pressure is held constant and the pressure at the discharge end is decreased, the flow of gas will increase up to a critical value. Beyond this point further decrease in the downstream pressure causes inflow. This is the critical flow condition.

When air flows through a nozzle, the critical condition is obtained if the upstream pressure is approximately two or more times the downstream pressure. The equation for critical flow through a nozzle is:

$$q = C_p A K \sqrt{MU/T}$$

where q is the mass rate of flow of the gas, C is a discharge coefficient, A is the cross-sectional area of the nozzle throat, p is the upstream static pressure of the gas, K is a dimensional coefficient involving the gas constant, M is the molecular weight of the gas, T is the absolute temperature of the gas upstream, and U is a constant that is characteristic of the gas equal to $k[2(k+1)]^8$, in which k is the ratio of specific heats ($C_p/C_v$) and s=(k+1)/(k−1).

For example, for air flow, this equation becomes:

$$q = 0.53 \, CpA / \sqrt{T}$$

where q is flow rate (lb/sec), C is discharge coefficient, p is pressure (psia), T is absolute temp (° K.), and A is nozzle area (sq. in.). A more detailed description of critical orifice behavior is provided in an article by H. P. Grace and C. E. Lapple, "Discharge Coefficients of Small Diameter Orifices and Flow Nozzles," Trns. ASME, Vol. 73, p. 639, July 1951.

In the preferred gas phase NVR monitor 60, the orifice 43 is operated in the critical flow regime, adding substantial advantage to the process 32 by which the sample gas 56 is precooled. In particular, operating the orifice 43 in the critical flow regime allows the downstream pressure $P_2$ to be adjusted independently of the flow F. As will be appreciated by those skilled in the art, $P_2$ the pressure immediately above the SAW resonator 52 is related to the average residence time of a molecule in the chamber enclosing the SAW resonator 52:

$$r = \frac{P_2 V_2}{kT_2 F}$$

where r is a unit of time, k is the Boltzman constant, and F is the flow rate in number of molecules per unit of time. The residence time R will influence the collection efficiency of the SAW resonator 52. For example, the residence time r should be adjusted such that the NVR molecule contacts the surface of the SAW resonator 52 a number of times such that the joint probability of "sticking" is near unity. Yet another significant advantage provided by the orifice 43 in a gas phase NVR monitor 60, is the minimal surface area presented to the gas 56 upon traversing into the volume $V_2$ surrounding the SAW resonator 52. Thus, using an orifice 43 for temperature and flow control also reduces contamination problems during sample gas delivery.

As described above in connection with FIG. 3, the NVR monitor is advantageously used to measure trace contaminants in a variety of sample fluids, including liquid. For optimal NVR monitor efficiency, the environmental conditions should be controlled and maintained to provide lower noise, higher collection efficiency, and more accurate knowledge of the collection efficiency for quantitative trace analysis. As shown schematically in FIG. 7, a preferred liquid phase NVR monitor 70 comprises the sensing SAW resonator 52 in contact with heat sink 46 which maintains the SAW sensor 52 at a preselected temperature $T_S$. In the NVR monitor 70, the reference SAW resonator 54 (not shown) is also maintained at the preselected temperature $T_S$. The sample fluid may be a liquid 55 such as a solvent, cleaning fluid, or processed liquid (e.g., isopropanol) useful for semiconductor integrated circuit fabrication. As discussed in connection with FIG. 1, the liquid 55 may be supplied from a bulk containment vessel 35 (FIG. 1) under pressure via a line 37. Alternatively, a specimen of the liquid may be manually transported from the vessel 35 to the sample reservoir 36. The liquid 55 is supplied to the SAW sensor 52 from sample reservoir 36. The process of supplying the sample liquid 55 to the SAW resonator 52 is schematically represented by the process box 39. In the preferred embodiment, the process 39 comprises metering a preselected volume $V_1$ of sample liquid, and more preferably also controlling the temperature $T_1$ of the sample liquid 55. The temperature of the sample liquid 55 is controlled by temperature controller 41 and may, for example, be adjusted to provide a temperature $T_1$ such that NVR is not deposited on the inner surfaces of the supply apparatus 45. Thus, supply process 39 should provide a known volume of liquid 55 from the sample reservoir 36. The supply mechanism comprises a micro-syringe 47 capable of delivering microliter quantities of liquid 56 to the SAW resonator 52. In one embodiment, the SAW resonator 52 has a recess 53 formed in the top surface to contain a measured amount of liquid 52.

Figure 7:
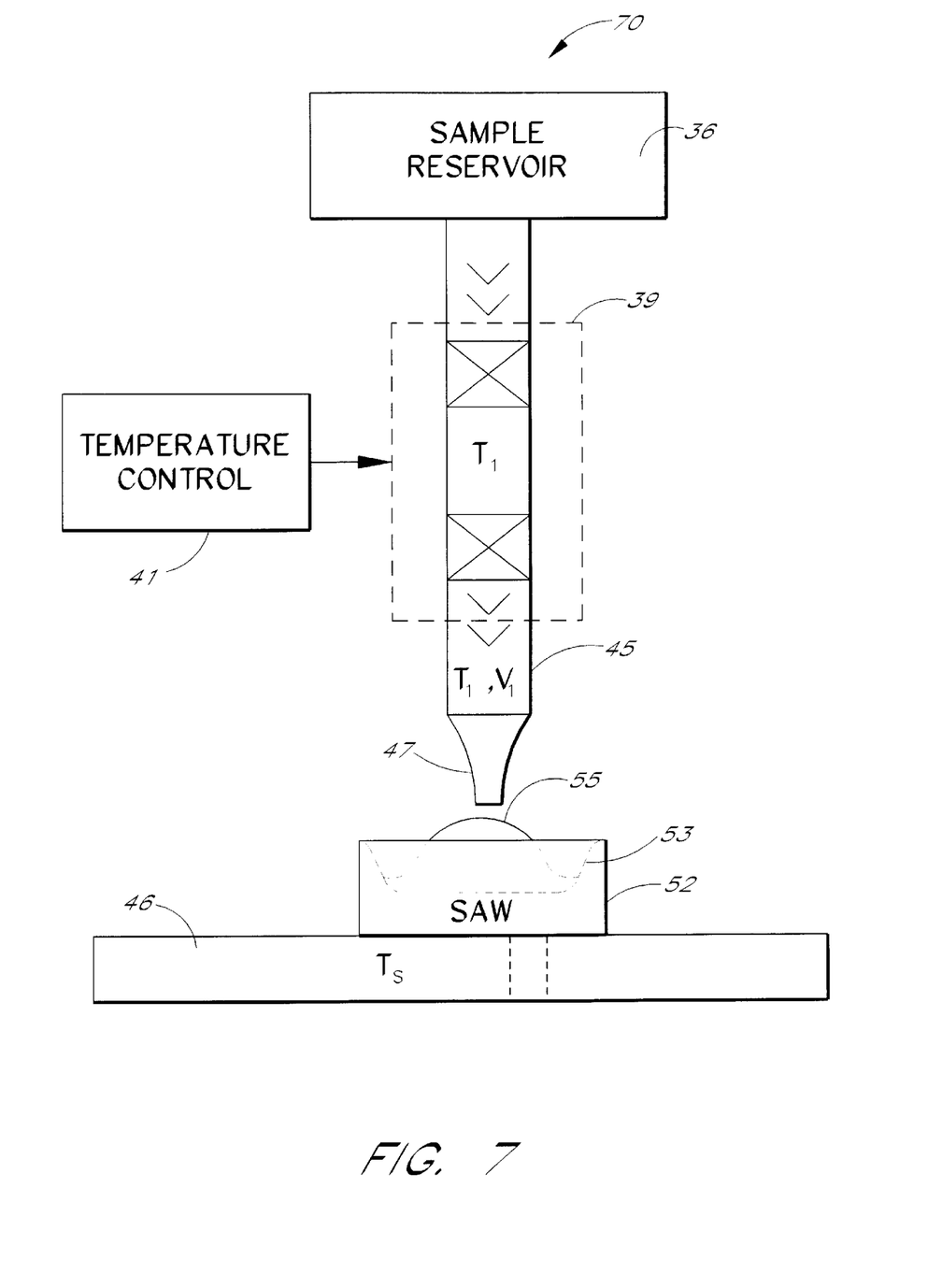
FIG. 7 is a schematic illustration of an embodiment of a liquid NVR monitor.

In operation, the temperature $T_S$ of the SAW resonator 52 is maintained at a value which selectively evaporates the carrier liquid, but not the NVR contained therein. Thus, substantially 100% collection efficiency is achieved. Since the volume of $V_1$ of the sample liquid 56 is known via the process 39, quantitative NVR analysis is possible. The ability to adjust the volume $V_1$ of the liquid 55 supplied to the SAW resonator is advantageous also from the perspective from operating the NVR monitor in different ways in accordance with the level of NVR contained in the fluid 55. For example, if it is known that small quantities of NVR are contained in the fluid, it may be preferable to initially supply a larger quantity of fluid allowing the fluid to evaporate and thereby depositing the NVR uniformly over the surface of the SAW resonator. Alternatively, if the level of NVR is large or unknown, it may be preferable to deposit small quantities of liquid 55 in several stages to ascertain the level of NVR to a point where sufficient or desired signal to noise ratio is obtained.

As with the gas phase NVR monitor, the liquid phase NVR monitor 70 may also be combined with other surface analysis techniques (previously discussed) so that the NVR may be characterized in terms of its atomic or molecular constitution.

Figure 8:
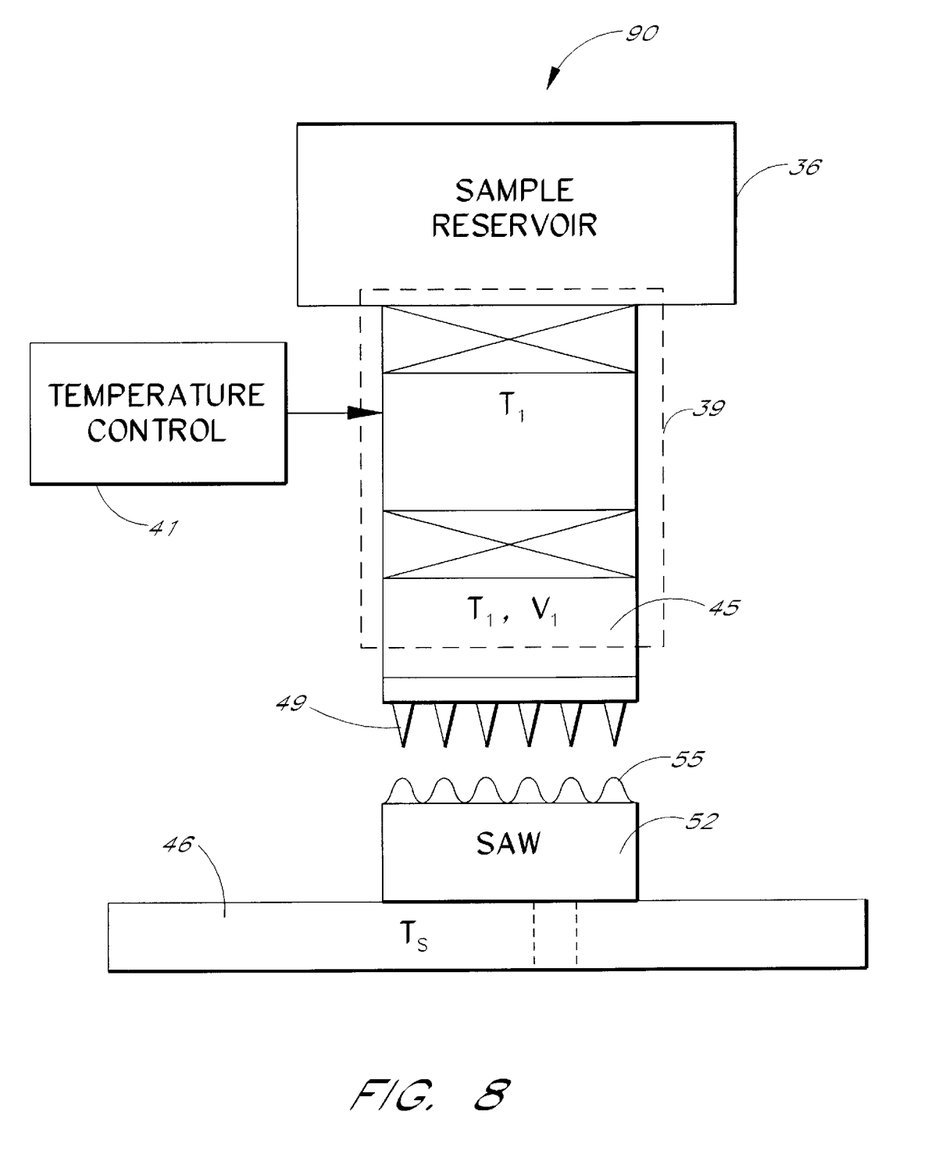
FIG. 8 is a schematic illustration of a preferred embodiment of a liquid NVR monitor.

Referring now to FIG. 8, another preferred liquid phase NVR monitor 90 comprises essentially all of the components shown previously in FIG. 7, except that the microsyringe 47 is replaced by an array of addressable liquid spray dispensers 49. In the present embodiment, the dispensers 49 comprise jets of the type used in ink jet print heads. The dispensing jets 49 deliver metered volumes of sample fluid 56 to positions on the surface of the SAW resonator 52 with a high degree of reproducibility. The array of independently addressable dispensers 49 shown in FIG. 8 distributes fluid layers of uniform thickness over the surface of the SAW resonator 52, providing accurate volume control and reproducible mass distribution.

An arrangement such as described in reference to FIG. 8 may also be used to apply coatings. In particular, the ink jet type dispensers would be ideal for applying chemical coatings of uniform thickness onto bare SAW sensors during production of the NVR instrument. These chemical coatings, as discussed above, are used to enhance diffusion of specific gases into the polymer coating the SAW sensor.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. An apparatus for detecting contaminants in an otherwise pure fluid contained in a vessel, comprising:

a SAW sensor having a sensor surface;

a fluid inlet adapted to receive a mixture of said contaminants and said otherwise pure fluid from said vessel at a pressure above atmospheric; and a fluid dispenser which receives the same mixture received by said inlet and dispenses said same mixture onto the SAW sensor surface such that the only contaminants dispensed onto said SAW sensor originate in said vessel.

2. The apparatus of claim 1, additionally comprising a temperature controller which controls the temperature of the mixture as said mixture flows from said fluid inlet to said fluid dispenser.

3. The apparatus of claim 1, additionally comprising a temperature controller comprising a heat sink in thermal contact with the SAW sensor and a thermoelectric element for heating and cooling the heat sink, the thermoelectric element in thermal contact with the heat sink.

4. The apparatus of claim 1, wherein the fluid comprises a compound of at least two elements.

5. The apparatus of claim 4, wherein said fluid compound comprises a halocarbon.

6. The apparatus of claim 5, wherein the halocarbon comprises a compound selected from the group consisting of $C_2F_6$, $CHF_3$, and $CF_4$.

7. The apparatus of claim 4, wherein the compound comprises $CO_2$.

8. The apparatus of claim 1, wherein the fluid comprises a gas, said fluid dispenser comprises a fluid conduit, said apparatus additionally comprising a pressure controller comprising an orifice disposed within the fluid conduit.

9. The apparatus of claim 8, wherein the fluid dispenser is arranged to direct the sample in a substantially linear path from said fluid dispenser to said sensor surface.

10. The apparatus of claim 1, wherein the fluid comprises a liquid.

11. The apparatus of claim 10, wherein the liquid comprises isopropanol.

12. The apparatus of claim 10, wherein the fluid dispenser comprises a liquid dispenser disposed adjacent to the sensor surface for supplying a preselected volume of liquid to the sensor surface.

13. The apparatus of claim 10, wherein the liquid dispenser comprises an array of jets disposed in proximity to the sensor surface.

14. The apparatus of claim 1, comprising a reference SAW sensor and a detection circuit, said detection circuit producing a signal corresponding to a frequency difference between outputs of the reference SAW sensor and the SAW sensor.

15. The apparatus of claim 1, wherein the contaminants comprise bulk containment contaminants.

16. The apparatus of claim 15, wherein the bulk containment contaminants comprise an oil.

17. The apparatus of claim 15, wherein the bulk containment contaminants comprise a lubricant.

18. The apparatus of claim 1 wherein said pressure is greater than 100 psi.

19. A method of detecting contaminants in an otherwise pure fluid, comprising:

transporting a mixture of said fluid and contaminants from a vessel into a fluid inlet of a detection apparatus at a pressure above atmospheric;

transporting said mixture from said fluid inlet along a flow path to a SAW sensor of said apparatus such that the only contaminants reaching said SAW sensor originate from said vessel;

delivering said mixture of said fluid and said contaminants from said flow path to said SAW sensor such that a surface of the SAW sensor is exposed to said mixture;

thermally separating the contaminants from the fluid in the delivered mixture such that said contaminants are distributed on the surface of the SAW sensor; and detecting changes in response of the SAW sensor due to the contaminants on the surface of the SAW sensor.

20. The method of claim 19, additionally comprising controlling the temperature of the mixture as said mixture flows along the flow path.

21. The method of claim 19, wherein the fluid comprises a liquid, and wherein the step of delivering comprises coating the surface of the SAW sensor with a uniformly thick layer of said liquid.

22. The method of claim 21, wherein the step of coating comprises spraying the liquid onto the surface of the SAW sensor.

23. The method of claim 19, wherein said vessel contains said mixture of said fluid and contaminants under pressure.

24. The method of claim 19, wherein the step of delivering the fluid to the SAW sensor comprises flowing the fluid through a fluid dispenser disposed adjacent to the surface of the SAW sensor such that the fluid travels in a substantially linear path from the fluid dispenser to the surface of the SAW sensor.

25. The method of claim 19, wherein the fluid comprises a liquid, and wherein the step of thermally separating the contaminants from the liquid comprises maintaining the SAW sensor at a temperature sufficient to induce evaporation of the liquid from the surface of the SAW sensor while leaving contaminants thereon.

26. The method of claim 19, wherein the fluid comprises a gas, and wherein the step of thermally separating the contaminants from the gas comprises maintaining the SAW sensor at a temperature sufficient to induce condensation of the contaminants onto the surface of the SAW sensor as the gas contacts the surface of the SAW sensor.

27. The method of claim 19, further comprising precooling the sample fluid prior to delivering the fluid to the SAW sensor.

28. The method of claim 27, wherein the step of precooling the sample fluid comprises substantially adiabatically cooling the sample fluid.

29. The method of claim 27, wherein the step of precooling the sample fluid comprises substantially isenthalpically cooling the sample fluid.

30. The method of claim 19, wherein the detecting step comprises detecting changes in frequency response of the SAW sensor by detecting a beat frequency between said SAW sensor and a reference sensor.

31. The method of claim 19, further comprising the step of identifying molecular species of the contaminants by determining a mass spectrum of the molecular species.

32. A method of detecting contaminants in an otherwise pure liquid, comprising:
   applying a mixture of said otherwise pure liquid and contaminants onto a surface of a SAW sensor, said applying including receiving said mixture from a container at a pressure above atmospheric and transporting said mixture from said container to said SAW sensor without modifying said mixture such that the only contaminants to be detected originate in said container;
   thermally separating the contaminants from the liquid such that the liquid is removed from the surface of the SAW sensor and the contaminants remain on the surface of the SAW sensor; and
   detecting changes in response of the SAW sensor due to the contaminants remaining on the surface of the SAW sensor.

33. The method of claim 32, wherein the step of applying the liquid comprises placing said liquid in a recess on the SAW sensor.

34. The method of claim 32, wherein the step of applying comprises spraying the liquid onto the SAW sensor.

35. The method of claim 32, further comprising the step of identifying molecular species of the contaminants by determining a mass spectrum of the molecular species.

36. An apparatus for detecting contaminants in an otherwise pure fluid contained in a vessel, comprising:
   a SAW sensor having a sensor surface;
   a fluid inlet adapted for connection to said vessel so as to receive a mixture of said contaminants and said otherwise pure fluid from said vessel at a pressure above atmospheric; and
   a fluid dispenser which receives the same mixture received by said inlet and dispenses said same mixture onto the SAW sensor surface such that the only contaminants dispensed onto said SAW sensor originate in said vessel, said apparatus non-selectively determining the presence of contaminants without regard to molecular species.

37. An apparatus for detecting contaminants in an otherwise pure liquid contained in a vessel, comprising:
   a SAW sensor having a sensor surface;
   a liquid inlet adapted for connection to said vessel so as to receive a mixture of said contaminants and said otherwise pure liquid from said vessel at a pressure above atmospheric; and
   a liquid dispenser which receives the same mixture received by said inlet and dispenses said same mixture onto the SAW sensor surface such that the only contaminants dispensed onto said SAW sensor originate in said vessel;
   a temperature controller that controls the temperature of said SAW sensor such that said contaminants are thermally separated from said liquid and distributed on the surface of the SAW sensor.

38. The apparatus of claim 37 additionally comprising a sample reservoir that receives said same mixture received by said inlet and supplies said same mixture to said fluid dispenser.

39. A method of detecting contaminants in an otherwise pure fluid, comprising:
   inputting a mixture of said otherwise pure fluid and contaminants into a fluid inlet of a detection apparatus from a container outside said detection apparatus at a pressure above atmospheric;
   transporting said mixture of said fluid and said contaminants from said fluid inlet along a flow path to a SAW sensor of said apparatus without modifying said mixture such that the only contaminants to be detected originate from said container;
   directing said mixture of said fluid and said contaminants from said flow path onto a surface of the SAW sensor;
   thermally separating the contaminants from the fluid such that said contaminants are distributed on the surface of the SAW sensor; and
   detecting changes in the response of the SAW sensor due to the contaminants on the surface of the SAW sensor.

40. The method of claim 39, wherein the fluid comprises a liquid and the temperature of the mixture is controlled as said mixture flows along the flow path such that said contaminants are not deposited on any surface prior to being delivered to said SAW sensor.

* * * * *